United States Patent
Winter

(10) Patent No.: US 6,337,426 B1
(45) Date of Patent: *Jan. 8, 2002

(54) ANTIFOULANT COMPOSITIONS AND PROCESSES

(75) Inventor: Roland A. E. Winter, Armonk, NY (US)

(73) Assignee: Nalco/Exxon Energy Chemicals, L.P., Sugarland, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/200,368

(22) Filed: Nov. 23, 1998

(51) Int. Cl.$^7$ ............................................. C10M 159/00
(52) U.S. Cl. ........................................... 585/5; 526/236
(58) Field of Search ............................... 585/5; 526/236

(56) References Cited

U.S. PATENT DOCUMENTS

| | | | |
|---|---|---|---|
| 4,670,131 A | 6/1987 | Ferrell | 208/48 |
| 5,282,957 A | 2/1994 | Wright et al. | 208/48 |
| 5,396,005 A | 3/1995 | Arhancet | 585/5 |
| 5,416,258 A | 5/1995 | Arhancet et al. | 585/5 |
| 5,711,767 A | 1/1998 | Gande et al. | 44/423 |

FOREIGN PATENT DOCUMENTS

| | | |
|---|---|---|
| DE | 1 944 233 | 8/1969 |
| DE | 19609312 A1 | 9/1997 |
| JP | 93/320217 | 12/1993 |
| WO | WO97/32833 | 9/1997 |

*Primary Examiner*—Peter D. Mulcahy
(74) *Attorney, Agent, or Firm*—Michael B. Martin; Thomas M. Breininger

(57) ABSTRACT

Industrial plant streams and processes that contain reactive light olefins such as isoprene and butadiene are plagued with fouling problems due to premature polymerization resulting in significant economic loss. A combination of phenylenediamines with nitroxides is found to be synergistic in its ability to prevent this premature polymerization of reactive light olefins.

18 Claims, No Drawings

ANTIFOULANT COMPOSITIONS AND PROCESSES

The present invention pertains to novel methods and compositions for inhibiting polymerization in industrial plant streams which contain reactive light olefins, thereby preventing fouling of processing equipment and of product in storage tanks. Particularly, the invention pertains to the use of a combination of phenylenediamines and nitroxides to prevent undesired polymerization in reactive light olefins.

BACKGROUND OF THE INVENTION

Industrial plant streams and processes which contain reactive light olefins are plagued with fouling problems due to unwanted polymerization. Examples of such plant streams and processes are hydrocarbon cracking processes in which light olefins are generated, industrial distillation processes of light olefin monomers, hydrogenation of light olefins and acetylenic compounds, and the like. Particular examples of such plant streams are depropanizer and debutanizer bottoms, light olefins typically generated in ethylene crackers. Such processes employ elevated temperatures which results in unwanted polymerization of the light olefin monomers. This unwanted polymerization results in the formation of deposits, or fouling, in distillation columns and other equipment such as heat transfer surfaces, reactor beds, reboilers, process lines, compressors, etc.

Fouling of the equipment or product during the stages of handling, processing, purification, and storage results in significant economic loss. Formation of deposits on heat transfer surfaces reduces process efficiency, and the unwanted polymerization also results in a loss of the desired product. Eventually the process must be stopped to clean the affected equipment.

To minimize fouling, commercial antifoulants are often added at 1–100 ppm levels at some point in the industrial process. Many classes of antifoulants are known, including phenylenediamines, hydroxylamines, nitroxides, and hindered phenols. However, fouling problems in reactive light olefin plant streams are not completely solved and industry continues to search for better solutions as well as for more cost effective ways to attack this problem.

Unexpectedly, the combination of phenylenediamines with nitroxides is found to be synergistic in its ability to prevent fouling in reactive light olefin streams. The activity of this combination exceeds that of state-of-the-art antifoulants. The state-of-the-art is described in the patents below, the relevant parts of which are incorporated herein by reference.

U.S. Pat. No. 4,670,131 discusses the use of any stable free radical to prevent polymerization in unsaturated organic feed streams. Specifically claimed is the prevention of fouling in olefinic feed streams by incorporation of a nitroxide at less than 700 ppb.

U.S. Pat. No. 5,282,957 discloses the use of hydroxyalkylhydroxylamine compounds to inhibit polymerization of hydrocarbon fluids containing dissolved oxygen.

U.S. Pat. No. 5,396,005 discloses the combination of a methoxyphenol, either eugenol or 2-t-butytl-4-hydroxyanisole, with a phenylenediamine to prevent polymerization of ethylenically unsaturated monomers.

U.S. Pat. No. 5,416,258 discusses the method of inhibiting polymerization of a butadiene-containing stream by the addition of a combination of a phenylenediamine and a hydroxytoluene compound.

The following patents teach the use of nitroxides as inhibitors in combination with coadditives to prevent polymerization in various systems. The coadditives include phenylenediamines.

JP 93/320217 discloses the use of nitroxides with coadditives in methacrylic acid. The coadditives are phenothiazines, aromatic amines, and phenols.

DE 19609312 A1 and related WO 97/32833 disclose the use of nitroxides as inhibitors for monomers in which the vinyl group is attached to a heteroatom. The compositions may additionally contain one or more costabilizers of the group of phenothiazines, quinones, hydroquinones and their ethers, hydroxylamines or phenylenediamines.

U.S. Pat. No. 5,711,767 discloses the use of nitroxides to prevent oxidative degradation and gum or deposit formation in gasoline. A costabilizer may also be employed which is selected from the group consisting of an aromatic amine, a phenolic antioxidant or a mixture of an aromatic amine and a phenolic antioxidant.

The synergistic activity of the combination of phenylenediamines with nitroxides towards preventing fouling in reactive light olefins is unknown. The superior performance of this particular combination to prevent premature polymerization in light olefins is not disclosed or suggested in the prior art.

DETAILED DESCRIPTION OF THE INVENTION

The present invention pertains to novel methods and compositions for preventing premature polymerization in industrial plant streams and processes containing reactive light olefins. The use of these novel methods and compositions prevents fouling of equipment and product during handling, processing, purification, and storage.

The novel compositions of this invention, stabilized against premature polymerization, comprise a) a light olefin monomer, and
   an effective polymerization inhibiting amount of
b) at least one phenylenediamine of the formula I

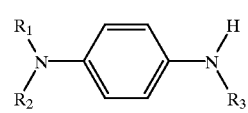

wherein $R_1$, $R_2$, and $R_3$ are the same or different and are hydrogen, straight or branched chain alkyl of 1 to 20 carbon atoms, straight or branched chain alkyl of 1 to 20 carbon atoms which is substituted by one to three aryl groups, aryl of 6 to 12 carbon atoms, or aryl of 6 to 12 carbon atoms which is substituted by one to three alkyl groups of 1 to 6 carbon atoms; and c) at least one nitroxide of the formula II

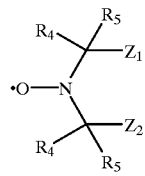

II wherein $R_4$ and $R_5$ are independently alkyl of 1 to 4 carbon atoms or are together pentamethylene; and $Z_1$ and $Z_2$ are each methyl or $Z_1$ and $Z_2$ together form a linking moiety which may or may not contain heteroatoms or carbonyl groups and which additionally may be substituted by hydroxy, cyanohydrin, amino, alkoxy, amido, ketal, carboxy, hydantoin, carbamate, or a urethane group.

The novel method of this invention comprises adding to a reactive light olefin an effective polymerization inhibiting amount of b) at least one phenylenediamine of the formula I

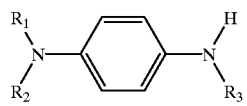

I wherein $R_1$, $R_2$, and $R_3$ are as defined previously; and c) at least one nitroxide of the formula II

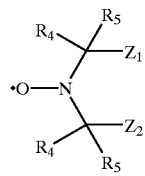

II wherein $R_4$, $R_5$, $Z_1$, and $Z_2$ are as defined previously.

The phenylenediamines of this invention have at least one N—H group. Preferred examples of phenylenediamines of this invention include N-phenyl-N'-methyl-1,4-phenylediamine, N-phenyl-N'-ethyl-1,4-phenylediamine, N-phenyl-N'-n-propyl-1,4-phenylediamine, N-phenyl-N'-isopropyl-1,4-phenylediamine, N-phenyl-N'-n-butyl-1,4-phenylediamine, N-phenyl-N'-iso-butyl-1,4-phenylediamine, N-phenyl-N'-sec-butyl-1,4-phenylediamine, N-phenyl-N'-t-butyl-1,4-phenylediamine, N-phenyl-N'-n-pentyl-1,4-phenylediamine, N-phenyl-N'-n-hexyl-1,4-phenylediamine, N-phenyl-N'-(1-methylhexyl)-1,4-phenylediamine, N-phenyl-N'-(1,3-dimethylbutyl)-1,4-phenylediamine, N-phenyl-N'-(1,4-dimethylpentyl)-1,4-phenylediamine, N-phenyl-N',N'-dimethyl-1,4-phenylenediamine, N-phenyl-N',N'-diethyl-1,4-phenylenediamine, N-phenyl-N',N'-di-n-butyl-1,4-phenylenediamine, N-phenyl-N',N'-di-sec-butyl-1,4-phenylenediamine, N-phenyl-N'-methyl-N'-ethyl-1,4-phenylenediamine, N,N'-dimethyl-1,4-phenylenediamine, N,N'-diethyl-1,4-phenylenediamine, N,N'-di-isopropyl-1,4-phenylenediamine, N,N'-di-iso-butyl-1,4-phenylenediamine, N,N'-di-sec-butyl-1,4-phenylenediamine, N,N'-bis(1,4-dimethylpentyl)-1,4-phenylenediamine, N,N'-bis(1,3-dimethylbutyl)-1,4-phenylenediamine, N,N'-diphenyl-1,4-phenylenediamine, N,N,N'-trimethyl-1,4-phenylenediamine, and N,N,N'-triethyl-1,4-phenylenediamine.

Particularly preferred examples of phenylenediamines of this invention include N,N'-di-sec-butyl-1,4-phenylenediamine, N,N'-bis(1,4-dimethylpentyl)-1,4-phenylenediamine, N,N'-di-iso-butyl-1,4-phenylenediamine, N,N'-bis(1,3-dimethylbutyl)-1,4-phenylenediamine, N-phenyl-N'-(1,4-dimethylpentyl)-1,4-phenylenediaamine, N-phenyl-N'-(1,3-dimethylbutyl)-1,4-phenylenediamine, N-phenyl-N'-iso-butyl-1,4-phenylenediamine, and N-phenyl-N'-sec-butyl-1,4-phenylenediamine.

Nitroxides of this invention have the general formula

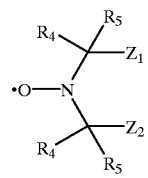

wherein $R_4$, $R_5$, $Z_1$, and $Z_2$ are as defined previously.

Preferably, the nitroxides of this invention have the formulae III, IV, V, VI, VII, VIII, and/or IX.

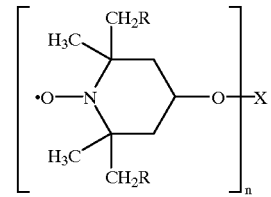

III

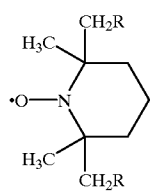

IV

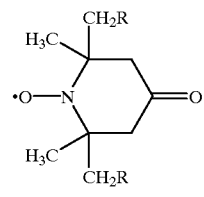

V

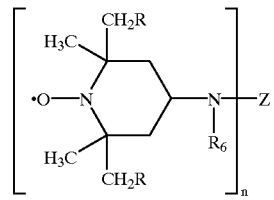

VI

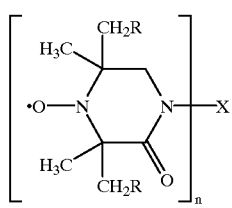

VII

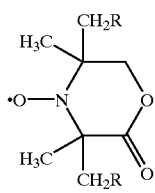

VIII

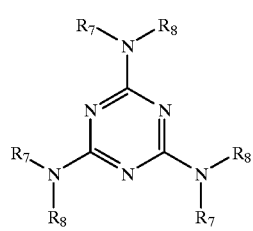

IX wherein

R is hydrogen or methyl, n is 1 or 2 in compounds of formula III, VI, and VII, when n is 1 in compounds of formulae III and VII, X is hydrogen; alkyl of 1 to 18 carbon atoms; alkanoyl of 2 to 18 carbon atoms; propargyl; glycidyl; benzoyl; phenyl; alkyl or alkanoyl of 2 to 50 carbon atoms interrupted by one to twenty —C=C—, —O—, —CO— and/or —COO— groups; alkyl of 1 to 50 carbon atoms or alkanoyl of 2 to 50 carbon atoms substituted by one to ten —OH and/or —COOY groups; alkyl or alkanoyl of 2 to 50 carbon atoms both interrupted by said —C=C—, —O—, —CO— and/or —COO— groups and substituted by said —OH and/or —COOY groups; cycloalkyl of 5 to 12 carbon atoms; cycloalkanoyl of 6 to 13 carbon atoms; or said cycloalkyl or cycloalkanoyl interrupted by one to six —C=C—, —O—, —CO— and/or —COO— groups; or said cycloalkyl or cycloalkanoyl substituted by one to six —OH and/or —COOY groups; or said cycloalkyl or cycloalkanoyl both interrupted by said —C=C—, —O—, —CO— and/or —COO— groups and substituted by said —OH and/or —COOY groups, Y is hydrogen, alkyl of 1 to 4 carbon atoms, or phenyl, when n is 2 in compounds of formulae III and VII, X is alkylene of 1 to 12 carbon atoms; alkylenoyl of 2 to 12 carbon atoms; alkylen-di-oyl of 2 to 12 carbon atoms; phenylene; phthaloyl; isophthaloyl; terephthaloyl; alkylene, alkylenoyl or alkylen-di-oyl of 2 to 50 carbon atoms interrupted by one to twenty —C=C—, —O—, —CO— and/or —COO— groups; alkylene of 1 to 50 carbon atoms, alkylenoyl of 2 to 50 carbon atoms or alkylen-di-oyl of 3 to 50 carbon atoms substituted by one to ten —OH and/or —COOY groups; alkylene or alkylenoyl of 2 to 50 carbon atoms, or alkylen-di-oyl of 3 to 50 carbon atoms both interrupted by said —C=C—, —O—, —CO— and/or —COO— groups and substituted by said —OH and/or —COOY groups; cycloalkylene of 5 to 12 carbon atoms; cycloalkylenoyl of 6 to 13 carbon atoms; cycloalkylen-di-oyl of 7 to 14 carbon atoms; or said cycloalkylene, cycloalkylenoyl or cycloalkylen-di-oyl interrupted by one to six —C=C—, —O—, —CO— and/or —COO— groups; or said cycloalkylene, cycloalkylenoyl or cycloalkylen-di-oyl substituted by one to six —OH and/or —COOY groups; or said cycloalkylene, cycloalkylenoyl or cycloalkylen-di-oyl both interrupted by said —C=C—, —O—, —CO— and/or —COO— groups and substituted by said —OH and/or —COOY groups, wherein Y has the same definition as above, in compounds of formula VI, $R_6$ is hydrogen, straight or branched chain alkyl of 1 to 20 carbon atoms, cycloalkyl of 5 to 12 carbon atoms, aralkyl of 7 to 15 carbon atoms, alkanoyl of 2 to 18 carbon atoms, alkenoyl of 3 to 18 carbon atoms or benzoyl, Z has the same meaning as for X above for when n is 1 or 2, or Z and $R_6$ together may form a cycloalkyl of 5 to 12 carbon atoms; cycloalkyl of 5 to 12 carbon atoms interrupted by one to six —C=C—, —O—, —CO— and/or —COO— groups; cycloalkyl of 5 to 12 carbon atoms substituted by one to six alkyl of 1 to 20 carbon atoms, alkenyl of 1 to 20 carbon atoms, —OH, and/or —COOY groups; or cycloalkyl of 5 to 12 carbon atoms both interrupted by said —C=C—, —O—, —CO— and/or —COO— groups and substituted by said alkyl, alkenyl, —OH, and/or —COOY groups, Y has the same meaning as above, in compounds of formula IX, each $R_7$ is independently hydrogen, straight or branched chain alkyl of 1 to 20 carbon atoms, or cycloalkyl of 5 to 12 carbon atoms, each $R_8$ is independently hydrogen, straight or branched chain alkyl of 1 to 20 carbon atoms, cycloalkyl of 5 to 12 carbon atoms, or a radical of the formula XI,

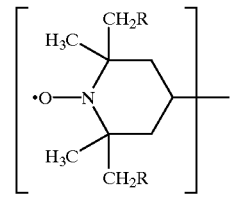

XI where R is as defined previously and with the proviso that at least one of the R groups is of formula XI.

Particularly preferred examples of nitroxides of this invention include bis(1-oxyl-2,2,6,6-tetramethylpiperidin-4-yl) sebacate, 4-hydroxy-1-oxyl-2,2,6,6-tetramethylpiperidine, 1-oxyl-2,2,6,6-tetramethylpiperidine, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetrametbylpiperidin-4-yl 4-t-butyl-benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6- tetramethylpiperidin-4-yl) hexahydroterephthalate, N,N'-bis (1-oxyl-2,2,6,6-tetramethylpiperidin-4-yl) adipamide, N-(1-oxyl-2,2,6,6-tetramethylpiperidin-4-yl) caprolactam, N-(1-oxyl-2,2,6,6-tetramethylpiperidin-4-yl) dodecylsuccinimide, 2,4,6-tris-[N-butyl-N-(1-oxyl-2,2,6,6-tetramethylpiperidin-4-yl)]-s-triazine, and 4,4'-ethylenebis (1-oxyl-2,2,6,6-tetramethylpiperidin-3-one).

The light olefins of this invention include hydrocarbon monomers generally having 2–6 carbon atoms. Examples are ethylene, propylene, butadiene, and isoprene.

The industrial plant streams are essentially the light olefins of this invention or they may additionally contain acetylenic compounds and/or saturated hydrocarbons. Examples of such streams are depropanizer and debutanizer bottoms which are generated in ethylene cracking processes.

The compositions of this invention are comprised of b) at least one phenylenediamine and c) at least one nitroxide, each as described supra. The inhibitor mixture may be added neat or it may be added as a solution in an appropriate hydrocarbon solvent. The components may be added separately or together as a mixture. The ratio of b) to c) employed is in the range of 1:10 to 10:1. The amount of components b) and c) necessary to prevent unwanted polymerization will depend on the temperature and duration of the particular process and may each be between 0.1 and 10,000 parts per million (ppm) based on the olefin. Preferably the amount used is between 0.1 and 100 ppm each on the olefin.

The industrial processes of this invention include any process in which a light olefin is handled or manipulated other than the intentional polymerization of the olefin. Such processes include but are not limited to hydrocarbon cracking processes, preheating, distillation, hydrogenation, extraction, etc.

The compositions and methods of this invention may also be used with other additives known to prevent fouling such as antioxidants, metal deactivators, corrosion inhibitors and the like. The stabilizer combination of this invention may be applied at any point in an industrial plant stream or process where it is effective.

Although specific embodiments of the present invention have been described in the detailed description above, the description is not intended to limit the invention to the particular forms or embodiments disclosed therein since they are to be recognized as illustrative rather than restrictive and it will be obvious to those skilled in the art that the invention is not so limited. Thus, the invention is declared to cover all changes and modifications of the specific examples of the invention herein disclosed for purposes of illustration which do not constitute departure from the spirit and scope of the invention. The embodiments of the invention in which a specific property or privilege is claimed are defined as follows.

The inhibitors used in the following Examples are:

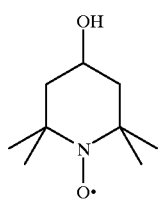

NO1

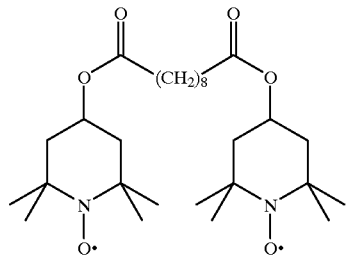

NO2

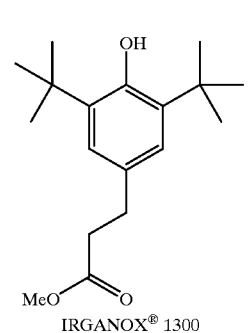

IRGANOX® 1300 (HP)

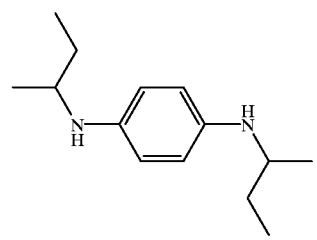

N,N'-Di-sec-butyl-1, 4-phenylenediamine (DBPDA)

EXAMPLE 1

Heat Induced Gum Test

The heat induced gum test utilizes heat under a nitrogen atmosphere to induce low molecular weight polymer formation (gum). The method is an adaptation of ASTM D 381, "Standard Test Method for Existent Gum in Fuels by Jet Evaporation," and D 873, "Standard Test Method for Oxidation Stability of Aviation Fuels (Potential Residue Method)."

Commercial isoprene is distilled in an inert atmosphere to obtain inhibitor-free isoprene which is stored under nitrogen below 0° C. until used. The diluent is ACS reagent grade toluene which is purged with nitrogen for 30 minutes prior to use. Nitrogen, not less than 99.6%, is used as the overpressure gas in the heat aging bomb and as the evaporation gas for gum determination. Inhibitor concentrations are reported in parts per million (ppm) by weight based on total hydrocarbons.

TABLE 1

Heat Induced Gum Content

| Trial | Isoprene (vol %) | Inhibitor | Conc. wt -ppm | Temp. (° F.) | Time (hours) | Gum Content (mg/100 mL) Insoluble | Soluble |
|---|---|---|---|---|---|---|---|
| a) | 50 | none | — | 212 | 4 | na* | 470 |
| b) | 50 | NO1 | 8 | 212 | 4 | 0 | 0 |
| c) | 50 | NO2 | 8 | 212 | 4 | 1 | 176 |
| d) | 50 | DBPDA | 9 | 212 | 4 | na* | 220 |
| e) | 50 | HP | 8 | 212 | 4 | 0 | 395 |
| f) | 50 | NO1<br>HP | 4<br>4 | 212 | 4 | 3 | 212 |
| g) | 50 | NO2<br>HP | 4<br>4 | 212 | 4 | 1 | 298 |
| h) | 50 | NO1<br>DBPDA | 2.7<br>1.3 | 212 | 4 | 0 | 0 |
| i) | 50 | NO1 | 4 | 212 | 4 | 2 | 212 |

*na = not available

It is seen from Table 1 that the combined use of the nitroxides and the phenylenediamines of the present invention provides a synergistic method for inhibiting polymerization of isoprene at elevated temperatures. Nitroxides and phenylenediamines each have an inhibiting effect, comparing b), c), d), and i) to the blank trial a). However trial h), in which a combination of a nitroxide with a phenylenediamine at a total level of 4 ppm was used had no gum formation. This was as good as double the amount of the nitroxide NO1 alone and far better than the use of 4 ppm of NO1 alone (trial i)) as well as far better than the use of more than double the amount of the phenylenediamine alone (trial d)). No such synergy is found with the combination of the nitroxides with other inhibitors of the prior art such as hindered phenols. The combinations of nitroxides with the hindered phenol IRGANOX® 1300 (HP) are not as good at inhibiting isoprene polymerization as the nitroxides alone (comparing trials f) and g) to b) and c)).

TABLE 2

Heat Induced Gum Content

| Trial | Isoprene (vol %) | Inhibitor | Conc. wt -ppm | Temp. (° F.) | Time (hours) | Gum Content (mg/100 mL) Insoluble | Soluble |
|---|---|---|---|---|---|---|---|
| j) | 50 | NO1<br>DBPDA | 5.3<br>2.7 | 248 | 4 | 1 | 893 |
| k) | 50 | NO1<br>DBPDA | 2.7<br>5.3 | 248 | 4 | 2 | 858 |
| l) | 50 | NO1 | 15 | 248 | 4 | 2 | 961 |
| m) | 50 | NO2 | 15 | 248 | 4 | 2 | 1258 |
| n) | 50 | NO1<br>NO2 | 7.5<br>7.5 | 248 | 4 | 0 | 1410 |
| o) | 50 | NO1<br>DBPDA | 5<br>10 | 248 | 4 | 0 | 352 |

Table 2 illustrates the synergistic polymerization inhibiting ability of the combination of nitroxides and phenylenediamines at 248° F. Note trials j) and k) perform better than l) at about one half the total loading of inhibitor. At equal total loading the performance of the combination of this invention is superior (trial o)).

TABLE 3

Heat Induced Gum Content

| Trial | Isoprene (vol %) | Inhibitor | Conc. wt -ppm | Temp. (° F.) | Time (hours) | Gum Content (mg/100 mL) Insoluble | Soluble |
|---|---|---|---|---|---|---|---|
| p) | 25 | NO1 | 3 | 248 | 2.5 | 6 | 264 |
| q) | 25 | NO1<br>DBPDA | 2<br>1 | 248 | 2.5 | 5 | 68 |

Table 3 illustrates the effectiveness of the use of low levels (3 ppm on total hydrocarbons) of inhibitor on dilute solutions of isoprene. The combined use of a nitroxide with a phenylenediamine as directed by this invention is superior at inhibiting polymer formation under these conditions.

EXAMPLE 2

Heat Induced Gum Test

The Heat Induced Gum Test is performed as in Example 1 replacing isoprene with 1,3-butadiene. The combined use of the nitroxides and phenylenediamines of the present invention provides a synergistic method for inhibiting polymerization of 1,3-butadiene at elevated temperatures.

Tables 1 through 3 illustrate the synergistic activity of a combination of a nitroxide and a phenylenediamine towards inhibiting polymerization of light olefins. This combination is superior to state of the art inhibitors. This provides for a more cost-effective method to prevent fouling in industrial plant streams and processes that involve the handling, storage, processing, and purification of reactive light olefins.

What is claimed is:

1. A composition stabilized against premature polymerization consisting of
    a) a light olefin monomer that optionally contains acetylenic compounds and/or one or more saturated hydrocarbons, and
    an effective polymerization inhibiting amount of a synergistic combination consisting of
    b) at least one phenylenediamine of the formula I

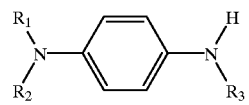

wherein $R_1$, $R_2$ and $R_3$ are the same or different and are hydrogen, straight or branched chain alkyl of 1 to 20 carbon atoms, straight or branched chain alkyl of 1 to 20 carbon atoms which is substituted by one to three aryl groups, aryl of 1 to 12 carbon atoms, or aryl of 1 to 12 carbon atoms which is substituted by one to three alkyl groups of 1 to 6 carbon atoms; and c) at least one nitroxide of the formula II

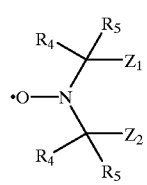

wherein $R_4$ and $R_5$ are independently alkyl of 1 to 4 carbon atoms or are together pentamethylene; and $Z_1$ and $Z_2$ are each methyl or $Z_1$ and $Z_2$ together form a linking moiety which may or may not contain heteroatoms or carbonyl groups and which additionally may be substituted by hydroxy, cyanohydrin, amino, alkoxy, amido, ketal, carboxy, hydantoin, carbamate, or a urethane group.

2. A composition according to claim 1 in which component b) is at least one phenylenediamine selected from N,N'di-sec-butyl-1,4-phenylenediamine, N,N'-bis(1,4-dimethylpentyl)-1,4-phenylenediamine, N,N'-di-iso-butyl-1,4-phenylenediamine, N,N'-bis(1,3-dimethylbutyl)-1,4-phenylenediamine, N-phenyl-N'-(1,4-dimethylpentyl)-1,4-phenylenediamine, N-phenyl-N'-(1,3-dimethylbutyl)-1,4-phenylenediamine, N-phenyl-N'-iso-butyl-1,4-phenylenediamine, and N-phenyl-N'-sec-butyl-1,4-phenylenediamine.

3. A composition according to claim 1 in which component c) is at least one nitroxide of the formulae III, IV, V, VI, VII, VIII, or IX

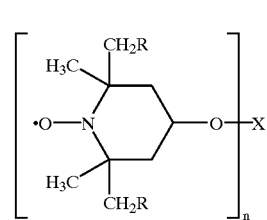

III

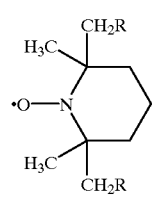

IV

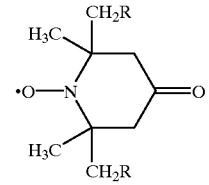

V

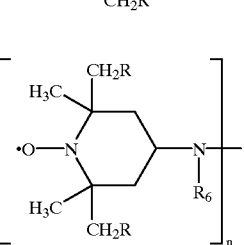

VI

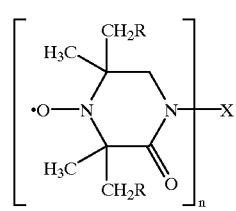

VII

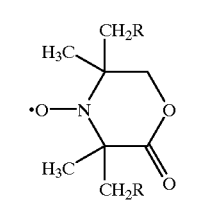

VIII

-continued

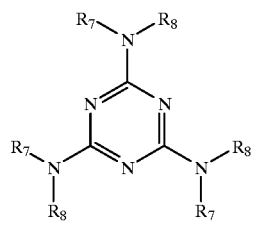

IX wherein

R is hydrogen or methyl, n is 1 or 2 in compounds of formula III, VI, and VII, when n is 1 in compounds of formulae III and VII, X is hydrogen; alkyl of 1 to 18 carbon atoms; alkanoyl of 2 to 18 carbon atoms; propargyl; glycidyl; benzoyl; phenyl; alkyl or alkanoyl of 2 to 50 carbon atoms interrupted by one to twenty —C=C—, —O—, —CO— and/or —COO— groups; alkyl of 1 to 50 carbon atoms or alkanoyl of 2 to 50 carbon atoms substituted by one to ten —OH and/or —COOY groups; alkyl or alkanoyl of 2 to 50 carbon atoms both interrupted by said —C=C—, —O—, —CO— and/or —COO— groups and substituted by said —OH and/or —COOY groups; cycloalkyl of 5 to 12 carbon atoms; cycloalkanoyl of 6 to 13 carbon atoms; or said cycloalkyl or cycloalkanoyl interrupted by one to six —C=C—, —O—, —CO— and/or —COO— groups; or said cycloalkyl or cycloalkanoyl substituted by one to six —OH and/or —COOY groups; or said cycloalkyl or cycloalkanoyl both interrupted by said —C=C—, —O—, —CO— and/or —COO— groups and substituted by said —OH and/or —COOY groups, Y is hydrogen, alkyl of 1 to 4 carbon atoms, or phenyl, when n is 2 in compounds of formulae III and VII, X is alkylene of 1 to 12 carbon atoms; alkylenoyl of 2 to 12 carbon atoms; alkylen-di-oyl of 2 to 12 carbon atoms; phenylene; phthaloyl; isophthaloyl; terephthaloyl; alkylene, alkylenoyl or alkylen-di-oyl of 2 to 50 carbon atoms interrupted by one to twenty —C=C—, —O—, —CO— and/or —COO— groups; alkylene of 1 to 50 carbon atoms, alkylenoyl of 2 to 50 carbon atoms or alkylen-di-oyl of 3 to 50 carbon atoms substituted by one to ten —OH and/or —COOY groups; alkylene or alkylenoyl of 2 to 50 carbon atoms, or alkylen-di-oyl of 3 to 50 carbon atoms both interrupted by said —C=C—, —O—, —CO— and/or —COO— groups and substituted by said —OH and/or —COOY groups; cycloalkylene of 5 to 12 carbon atoms; cycloalkylenoyl of 6 to 13 carbon atoms; cycloalkylen-di-oyl of 7 to 14 carbon atoms; or said cycloalkylene, cycloalkylenoyl or cycloalkylen-di-oyl interrupted by one to six —C=C—, —O—, —CO— and/or —COO— groups; or said cycloalkylene, cycloalkylenoyl or cycloalkylen-di-oyl substituted by one to six —OH and/or —COOY groups; or said cycloalkylene, cycloalkylenoyl or cycloalkylen-di-oyl both interrupted by said —C=C—, —O—, —CO— and/or —COO— groups and substituted by said —OH and/or —COOY groups, wherein Y has the same definition as above, in compounds of formula VI, $R_6$ is hydrogen, straight or branched chain alkyl of 1 to 20 carbon atoms, cycloalkyl of 5 to 12 carbon atoms, aralkyl of 7 to 15 carbon atoms, alkanoyl of 2 to 18 carbon atoms, alkenoyl of 3 to 18 carbon atoms or benzoyl, Z has the same meaning as for X above for when n is 1 or 2, or Z and $R_6$ together may form a cycloalkyl of 5 to 12 carbon atoms; cycloalkyl of 5 to 12 carbon atoms interrupted by one to six —C=C—, —O—, —CO— and/or —COO— groups; cycloalkyl of 5 to 12 carbon atoms substituted by one to six alkyl of 1 to 20 carbon atoms, alkenyl of 1 to 20 carbon atoms, —OH, and/or —COOY groups; or cycloalkyl of 5 to 12 carbon atoms both interrupted by said —C=C—, —O—, —CO— and/or —COO— groups and substituted by said alkyl, alkenyl, —OH, and/or —COOY groups, Y has the same meaning as above, in compounds of formula IX, each $R_7$ is independently hydrogen, straight or branched chain alkyl of 1 to 20 carbon atoms, or cycloalkyl of 5 to 12 carbon atoms, each $R_8$ is independently hydrogen, straight or branched chain alkyl of 1 to 20 carbon atoms, cycloalkyl of 5 to 12 carbon atoms, or a radical of the formula XI,

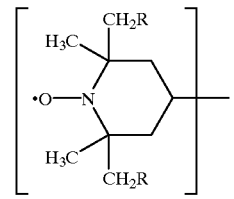

XI where R is as defined previously and with the proviso that at least one of the $R_8$ groups is of formula XI.

4. A composition according to claim 1 in which component c) is at least one nitroxide selected from bis(1-oxyl-2,2,6,6-tetramethylpiperidin-4-yl) sebacate, 4-hydroxy-1-oxyl-2,2,6,6-tetramethylpiperidine, 1-oxyl-2,2,6,6-tetramethylpiperidine, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-t-butyl-benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl)-n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, N-(1-oxyl-2,2,6,6-tetramethylpiperidin-4-yl) caprolactam, N-(1-oxyl-2,2,6,6-tetramethylpiperidin-4-yl) dodecylsuccinimide, 2,4,6-tris-[N-butyl-N-(1-oxyl-2,2,6,6-tetramethylpiperidin-4-yl)]-s-triazine, and 4,4'-ethylenebis(1-oxyl-2,2,6,6-tetramethylpiperidin-3-one).

5. A composition according to claim 1 in which the ratio of components b) to c) is in the range of 1:10 to 10:1.

6. A composition according to claim 1 in which components b) and c) are each present in the range of from about 0.1 parts per million to about 10,000 parts per million of component a).

7. A composition according to claim 1 in which component a) has 2 to 6 carbon atoms.

8. A composition according to claim 1 in which component a) is ethylene, propylene, butadiene, or isoprene.

9. A method for inhibiting the premature polymerization of reactive light olefins consisting of adding to said olefins an effective polymerization inhibiting amount of a synergistic combination consisting of a) at least one phenylenediamine of the formula I

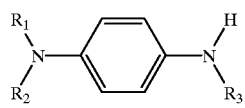

I wherein $R_1$, $R_2$ and $R_3$ are the same or different and are hydrogen, straight or branched chain alkyl of 1 to 20 carbon atoms, straight or branched chain alkyl of 1 to 20 carbon atoms which is substituted by one to three aryl groups, aryl of 1 to 12 carbon atoms, or aryl of 1 to 12 carbon atoms which is substituted by one to three alkyl groups of 1 to 6 carbon atoms; and b) at least one nitroxide of the formula II

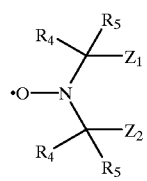

II wherein $R_4$ and $R_5$ are independently alkyl of 1 to 4 carbon atoms or are together pentamethylene; and $Z_1$ and $Z_2$ are each methyl or $Z_1$ and $Z_2$ together form a linking moiety which may or may not contain heteroatoms or carbonyl groups and which additionally may be substituted by hydroxy, cyanohydrin, amino, alkoxy, amido, ketal, carboxy, hydantoin, carbamate, or a urethane group.

10. A method according to claim 9 in which component b) is at least one phenylenediamine selected from N,N'-di-sec-butyl-1,4-phenylenediamine, N,N'-bis(1,4-dimethylpentyl)-1,4-phenylenediamine, N,N'-di-iso-butyl-1,4-phenylenediamine, N,N'-bis(1,3-dimethylbutyl)-1,4-phenylenediamine, N-phenyl-N'-(1,4-dimethylpentyl)-1,4-phenylenediamine, N-phenyl-N'-(1,3-dimethylbutyl)-1,4-phenylenediamine, N-phenyl-N'-iso-butyl-1,4-phenylenediamine, and N-phenyl-N'-sec-butyl-1,4-phenylenediamine.

11. A method according to claim 9 in which component c) is at least one nitroxide of the formulae III, IV, V, VI, VII, VIII or IX

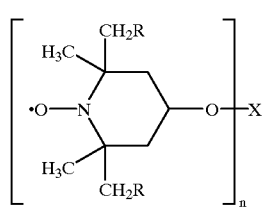

III

-continued

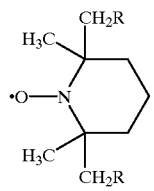

IV

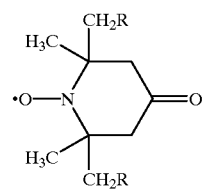

V

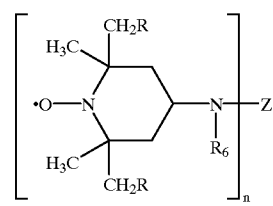

VI

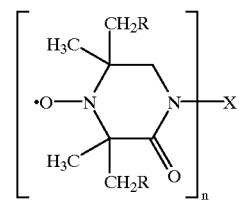

VII

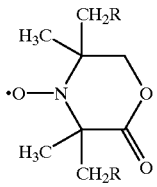

VIII

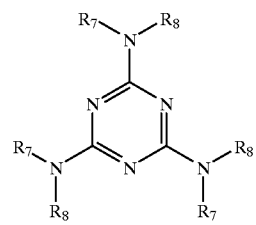

IX wherein
R is hydrogen or methyl,
n is 1 or 2 in compounds of formula III, VI, and VII,
when n is 1 in compounds of formulae III and VII,
X is hydrogen; alkyl of 1 to 18 carbon atoms; alkanoyl of 2 to 18 carbon atoms; propargyl; glycidyl; benzoyl; phenyl; alkyl or alkanoyl of 2 to 50 carbon atoms interrupted by one to twenty —C=C—, —O—, —CO— and/or —COO— groups; alkyl of 1 to 50 carbon atoms or alkanoyl of 2 to 50 carbon atoms substituted by one to ten —OH and/or —COOY groups; alkyl or alkanoyl of 2 to 50 carbon atoms both interrupted by said —C=C—, —O—, —CO— and/or —COO— groups and substituted by said —OH and/or —COOY groups; cycloalkyl of 5 to 12 carbon atoms; cycloalkanoyl of 6 to 13 carbon atoms; or said cycloalkyl or cycloalkanoyl interrupted by one to six —C=C—, —O—, —CO— and/or —COO— groups; or said cycloalkyl or cycloalkanoyl substituted by one to six —OH and/or —COOY groups; or said cycloalkyl or cycloalkanoyl both interrupted by said —C=C—, —O—, —CO— and/or —COO— groups and substituted by said —OH and/or —COOY groups, Y is hydrogen, alkyl of 1 to 4 carbon atoms, or phenyl, when n is 2 in compounds of formulae III and VII, X is alkylene of 1 to 12 carbon atoms; alkylenoyl of 2 to 12 carbon atoms; alkylen-di-oyl of 2 to 12 carbon atoms; phenylene; phthaloyl; isophthaloyl; terephthaloyl; alkylene, alkylenoyl or alkylen-di-oyl of 2 to 50 carbon atoms interrupted by one to twenty —C=C—, —O—, —CO— and/or —COO— groups; alkylene of 1 to 50 carbon atoms, alkylenoyl of 2 to 50 carbon atoms or alkylen-di-oyl of 3 to 50 carbon atoms substituted by one to ten —OH and/or —COOY groups; alkylene or alkylenoyl of 2 to 50 carbon atoms, or alkylen-di-oyl of 3 to 50 carbon atoms both interrupted by said —C=C—, —O—, —CO— and/or —COO— groups and substituted by said —OH and/or —COOY groups; cycloalkylene of 5 to 12 carbon atoms; cycloalkylenoyl of 6 to 13 carbon atoms; cycloalkylen-di-oyl of 7 to 14 carbon atoms; or said cycloalkylene, cycloalkylenoyl or cycloalkylen-di-oyl interrupted by one to six —C=C—, —O—, —CO— and/or —COO— groups; or said cycloalkylene, cycloalkylenoyl or cycloalkylen-di-oyl substituted by one to six —OH and/or —COOY groups; or said cycloalkylene, cycloalkylenoyl or cycloalkylen-di-oyl both interrupted by said —C=C—, —O—, —CO— and/or —COO— groups and substituted by said —OH and/or —COOY groups, wherein Y has the same definition as above, in compounds of formula VI, $R_6$ is hydrogen, straight or branched chain alkyl of 1 to 20 carbon atoms, cycloalkyl of 5 to 12 carbon atoms, aralkyl of 7 to 15 carbon atoms, alkanoyl of 2 to 18 carbon atoms, alkenoyl of 3 to 18 carbon atoms or benzoyl, Z has the same meaning as for X above for when n is 1 or 2, or Z and & together may form a cycloalkyl of 5 to 12 carbon atoms; cycloalkyl of 5 to 12 carbon atoms interrupted by one to six —C=C—, —O—, —CO— and/or —COO— groups; cycloalkyl of 5 to 12 carbon atoms substituted by one to six alkyl of 1 to 20 carbon atoms, alkenyl of 1 to 20 carbon atoms, —OH, and/or —COOY groups; or cycloalkyl of 5 to 12 carbon atoms both interrupted by said —C=C—, —O—, —CO— and/or —COO— groups and substituted by said alkyl, alkenyl, —OH, and/or —COOY groups, Y has the same meaning as above, in compounds of formula IX, each $R_7$ is independently hydrogen, straight or branched chain alkyl of 1 to 20 carbon atoms, or cycloalkyl of 5 to 12 carbon atoms, each $R_8$ is independently hydrogen, straight or branched chain alkyl of 1 to 20 carbon atoms, cycloalkyl of 5 to 12 carbon atoms, or a radical of the formula XI,

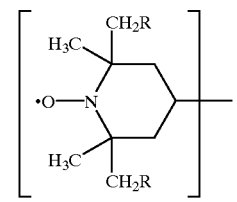

where R is as defined previously and with the proviso that at least one of the $R_8$ groups is of formula XI.

12. A method according to claim 9 in which component c) is at least one nitroxide selected from bis(1-oxyl-2,2,6,6-tetramethylpiperidin-4-yl) sebacate, 4-hydroxy-1-oxyl-2,2,6,6-tetramethylpiperidine, 1-oxyl-2,2,6,6-tetramethylpiperidine, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-t-butyl-benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis (1-oxyl-2,2,6,6-tetramethylpiperidin-4-yl) adipamide, N-(1-oxyl-2,2,6,6-tetramethylpiperidin-4-yl) caprolactam, N-(1-oxyl-2,2,6,6-tetramethylpiperidin-4-yl) dodecylsuccinimide, 2,4,6-tris-[N-butyl-N-(1-oxyl-2,2,6,6-tetramethylpiperidin-4-yl)]-s-triazine, and 4,4'-ethylenebis (1-oxyl-2,2,6,6-tetramethylpiperidin-3-one).

13. A method according to claim 9 in which components b) and c) are each added to said olefin in an amount ranging from about 0.1 part per million to about 10,000 parts per million olefin.

14. A method according to claim 9 in which the light olefins are hydrocarbon monomers having 2 to 6 carbon atoms.

15. A method according to claim 9 in which the light olefin is ethylene, propylene, butadiene or isoprene.

16. A method according to claim 9 in which the light olefins additionally contain acetylenic compounds and/or one or more saturated hydrocarbons.

17. A method according to claim 9 in which components b) and c) are added in a hydrocarbon solvent.

18. A method according to claim 9 in which components b) and c) are added in the ratio of 1:10 to 10:1.

* * * * *